(12) United States Patent
Kwon et al.

(10) Patent No.: US 9,448,154 B2
(45) Date of Patent: Sep. 20, 2016

(54) SYSTEMS AND METHODS FOR TESTING IGNITION PROPERTIES OF PARTICLES

(71) Applicant: The Boeing Company, Seal Beach, CA (US)

(72) Inventors: Eddie Kwon, Seattle, WA (US); John Jefferson Odell, Pasadena, CA (US)

(73) Assignee: The Boeing Company, Chicago, IL (US)

( * ) Notice: Subject to any disclaimer, the term of this patent is extended or adjusted under 35 U.S.C. 154(b) by 99 days.

(21) Appl. No.: 13/891,385

(22) Filed: May 10, 2013

(65) Prior Publication Data

US 2014/0331743 A1 Nov. 13, 2014

(51) Int. Cl.
*G01N 15/10* (2006.01)
*G01N 25/50* (2006.01)

(52) U.S. Cl.
CPC ............. *G01N 15/10* (2013.01); *G01N 25/50* (2013.01)

(58) Field of Classification Search
CPC ..... G01N 15/10; G01N 25/50; G01N 33/227
See application file for complete search history.

(56) References Cited

U.S. PATENT DOCUMENTS 3,407,653 A * 10/1968 Harp, Jr. .................... 73/147

OTHER PUBLICATIONS

Non-Patent Literature Windshear, found at www.windshearinc.com/news_mar08.asp, archived on Nov. 26, 2011.*

European Search Report for related European Patent Application No. EP 14 16 2030, Jun. 18, 2014.
Fereres et al., "Mass flux at ignition in reduced pressure environments," Combustion and Flame, vol. 158, pp. 1301-1306, Nov. 25, 2010.
Gao et al., "Theoretical and Experimental Study on Spontaneous Ignition of Lignite during the Drying Process in a Packed Bed," Energy & Fuels, vol. 26, pp. 6876-6887, Oct. 9, 2012.
Laurendeau et al., "Thermal Ignition of Methane-Air Mixtures by Hot Surfaces: A Critical Examination," Combustion and Flame, vol. 46, pp. 29-49, Jan. 1, 1982.
Stamatov et al., "Explosions of methane/air mixtures induced by radiation-heated large inert particles," Fuel, vol. 84, pp. 2086-2092, Apr. 21, 2005.
Coronel et al., "Ignition of n-Hexane-Air Mixtures by Moving Hot Spheres," 24$^{th}$ ICDERS—International Colloquium on the Dynamics of Explosions and Reactive Systems, Taipei, Taiwan, Jul. 28-Aug. 2, 2013.
Bothe et al, The Safe Use of Optics in Potentially Explosive Atmospheres, London : IEE, Explosion Safety in Hazardous Areas, 44-49 (1999).
Colwell et al., Hot Surface Ignition of Automotive and Aviation Fluids, Fire Technology, 41, 105-123 (2005).

(Continued)

*Primary Examiner* — Laura Martin
*Assistant Examiner* — Irving A Campbell
(74) *Attorney, Agent, or Firm* — DASCENZO Intellectual Property Law, P.C.

(57) ABSTRACT

Systems and methods for testing ignition properties of particles in a gas. Systems include a test chamber sized to hold a particle to be tested, a gas supply configured to deliver a gas to the test chamber, a heating device configured to heat the particle, and data acquisition equipment configured to collect data associated with the particle and/or the gas. Methods include generating a flow of gas around a particle that is fixed in space relative to the flow of gas in a test chamber, heating the particle and/or heating the gas, and collecting data associated with the particle and/or the gas.

25 Claims, 3 Drawing Sheets

(56) References Cited

OTHER PUBLICATIONS

Hawksworth et al., Ignition of Explosive Atmospheres by Mechanical Equipment, Manchester : Institution of Chemical Engineers, Hazards XVIII (2004).

Kuchta et al., Hot Gas Ignition Temperatures of Hydrocarbon Fuel Vapor-Air Mixtures, Int. Bu. of Mines, Report of Investigations 6857 (1966).

Rogers et al., Ignition of Dust Clouds and Dust Deposits by Friction Sparks and Hotspots, Manchester : Institution of Chemical Engineers, Hazards, XIX (2006).

Welzel et al., Ignition of Combustible/Air Mixtures by Small Radiatively Heated Surfaces, Journal of Hazardous Materials A72,1-9 (2000).

Search Report and Written Opinion, Canadian Intellectual Property Office, Jul. 5, 2015.

European Patent Office, Extended European Search Report for related European patent application EP 14 162 030.2, Mar. 30, 2016.

Stewart Paterson, "*Ignition of inflammable gases by hot moving particles II,*" The London, Edinburgh, and Dublin Philosophical Magazine and Journal of Science, vol. 30, pp. 437-457, Jul. 1, 1940.

Robert S. Silver, "*The ignition of gaseous mixtures by hot particles,*" The London, Edinburgh, and Dublin Philosophical Magazine and Journal of Science, vol. 23, No. 156, pp. 633-657, Apr. 1, 1937.

Canadian Intellectual Property Office, Office action for related Canadian patent application 2,844,182, Apr. 27, 2016.

\* cited by examiner

SYSTEMS AND METHODS FOR TESTING IGNITION PROPERTIES OF PARTICLES

FIELD

The present disclosure relates to systems and method for testing ignition properties of particles.

BACKGROUND

Various environments present risks associated with the combustion of a volume of gas, such as when triggered by a hot particle passing into and/or through the volume of gas. For example, an impact spark or sparks from machinery operating in an underground mining facility may ignite gases that are present. Combustion of dust in a grain silo may be triggered by hot particles. These and other scenarios have heretofore not been able to be simulated in a controlled testing environment. Previously, only stationary particles in generally stagnant volumes of gas have been studied.

SUMMARY

Systems and methods for testing ignition properties of particles are disclosed herein. Methods according to the present disclosure include generating a flow of gas around a particle that is fixed in space relative to the flow of gas in a test chamber, heating the particle and/or heating the gas to a temperature, and collecting data associated with the particle and/or the flow of gas. Systems according to the present disclosure include a test chamber sized to hold a particle to be tested, a gas supply configured to deliver a gas to the test chamber, a heating device configured to heat the particle, and data acquisition equipment configured to collect data associated with the particle and/or the gas.

DESCRIPTION

Systems and methods for testing ignition properties of particles are disclosed herein and may be used to simulate various predefined scenarios and to build, maintain, and utilize a database of models associated with various environments in which particles travel in, or are otherwise exposed to, gases and in which a risk of combustion of the particle and/or the gas may be present. In other words, as used herein, the ignition properties of a particle relate to the combustion of the particle itself and/or to the combustion of the gas within which the particle is present, and may be a function of such variables as the material composition of the particle, the size of the particle, the shape of the particle, the surface characteristics of the particle, the temperature the particle, the velocity of the particle relative to the gas, the composition of the gas, the pressure of the gas, the temperature of the gas, the velocity of the gas relative to the particle, the flow characteristics of the gas around the particle, etc.

An illustrative, non-exclusive example of an aerospace scenario that may be simulated by a system and/or method according to the present disclosure relates to lightning strikes of aircraft at altitude. When lightning strikes an aircraft, and when the electricity associated with the lightning strike is dispersed across the structure of the aircraft, there is a risk that a small particle of material may be discharged from structure of the aircraft. Systems and methods according to the present disclosure may be used to help understand and to study and model the ignition thresholds of various gases based on properties of the discharged particle.

Other scenarios and environments that may be simulated by systems and models according to the present disclosure include any relevant environment in which a risk of combustion is associated with particles traveling into and/or through a volume of gas. For example, in addition to various aerospace scenarios, it may be desirable to simulate scenarios associated with industrial environments, agricultural environments, various environments where fuel fumes are present, various environments where combustible gases are present, various environments where hot particles move through a gas, etc.

Figure 1:
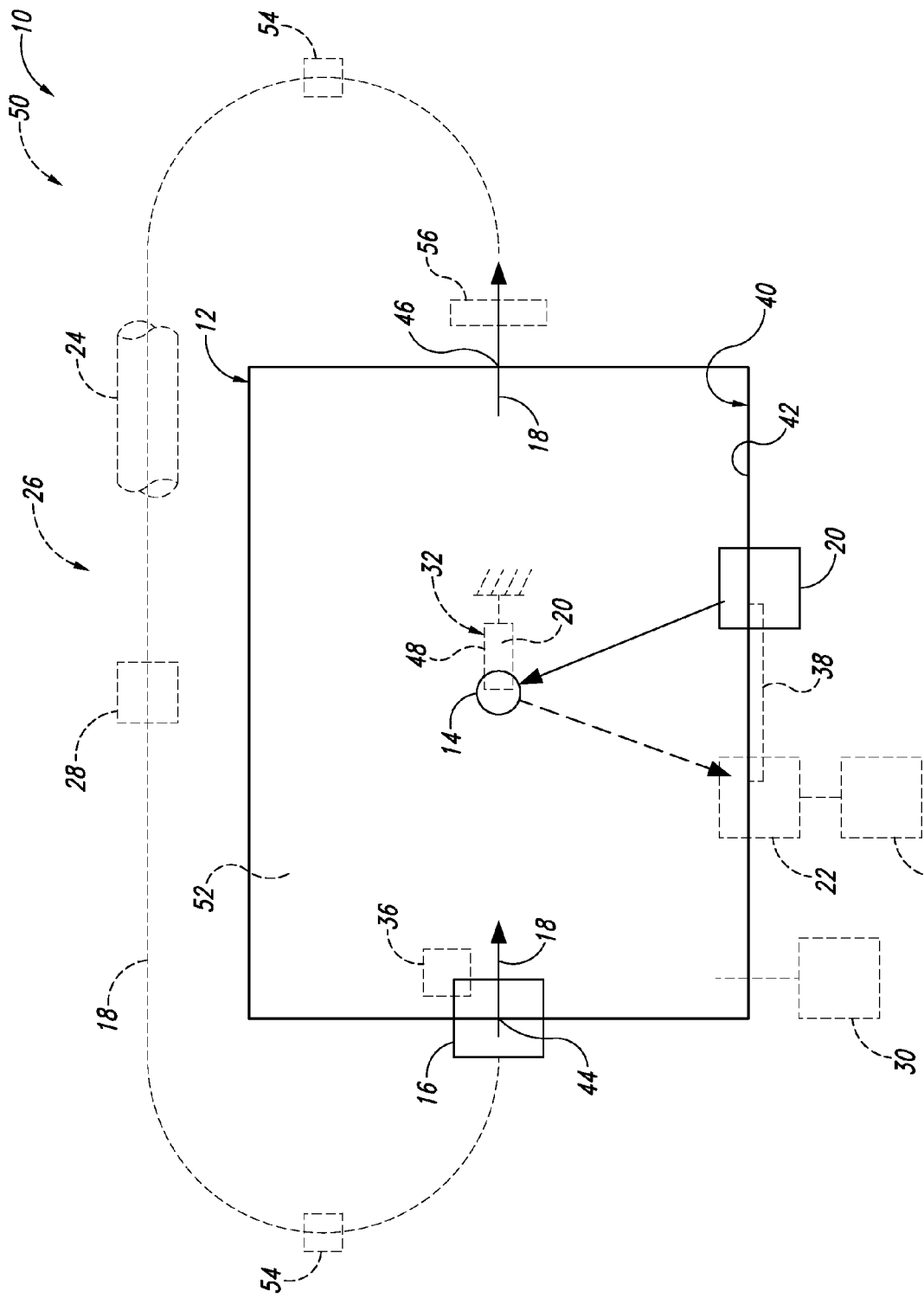
FIG. 1 is a schematic diagram representing systems for testing ignition properties of particles.
Figure 2:
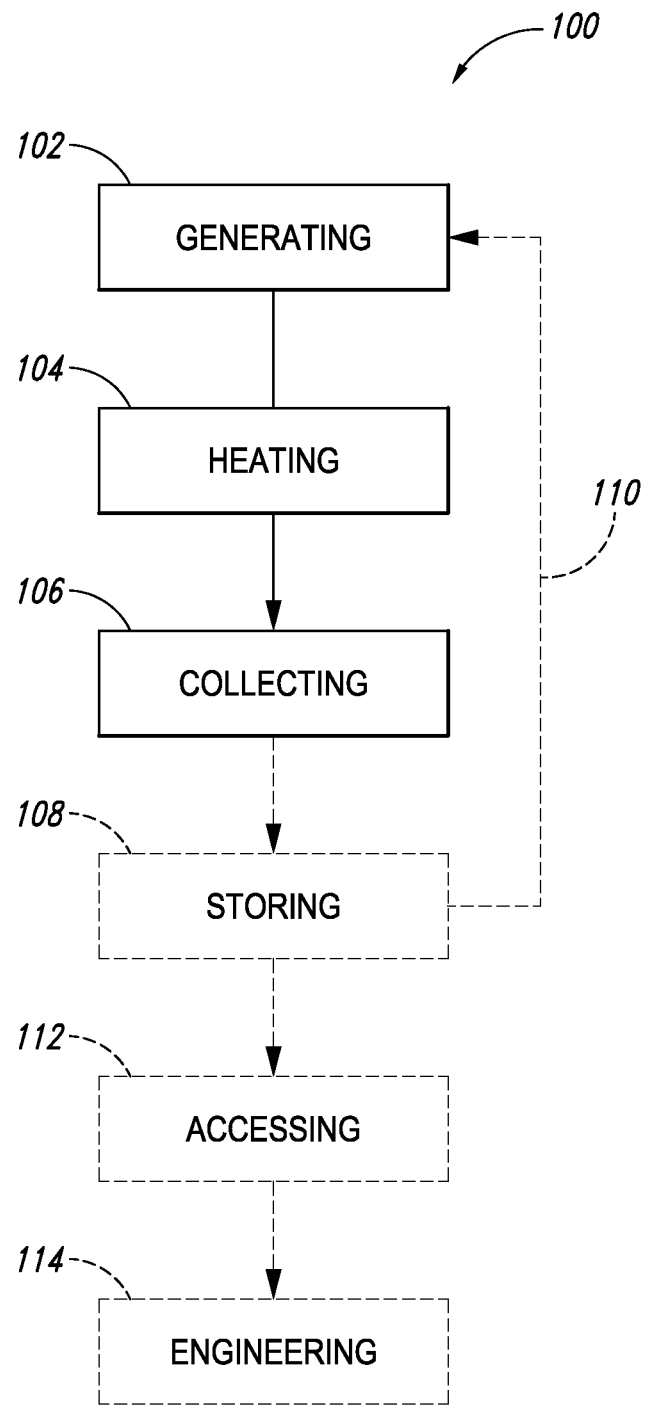
FIG. 2 is a flowchart schematically representing methods for testing ignition properties of particles.

FIG. 1 provides a schematic representation of examples of systems 10 for testing ignition properties of particles, and FIG. 2 provides a flowchart schematically representing examples of methods 100 for testing ignition properties of particles. In FIGS. 1-2, some elements are illustrated in dashed lines, schematically representing that such elements may be optional or may correspond to an optional version of a system 10 and/or a method 100. That said, not all systems 10 and methods 100 are required to include the elements illustrated in solid lines. The schematic representation of systems 10 and methods 100 in FIGS. 1-2 are not limiting and other systems 10, component parts of systems 10, methods 100, and steps of methods 100 are within the scope of the present disclosure, including systems 10 having greater than or fewer than the number of illustrated elements, as well as methods 100 having greater than or fewer than the number of illustrated steps, as understood from the discussions herein. As also understood from the discussions herein, methods 100 are not required to have the schematically represented steps of FIG. 2 performed in the order illustrated. Moreover, a system 10 is not required to implement or otherwise utilize a method 100, and a method 100 is not required to utilize a system 10 in all examples of systems 10 and methods 100 according to the present disclosure.

With initial reference to FIG. 1, a system 10 may include at least a test chamber 12 sized to hold a particle 14 to be tested, a gas supply 16 configured to deliver a gas 18 to the test chamber, a heating device 20 configured to heat the particle, and data acquisition equipment 22 configured to collect data associated with the particle and/or the gas. Additionally, as schematically and optionally illustrated in FIG. 1, in some embodiments, a system 10 further may include one or more of ducting 24 that defines a closed-loop conduit 26 that includes the test chamber, a fan 28 configured to channel gas through the ducting and around a particle held in the test chamber, a vacuum system 30 configured to draw a vacuum in at least the test chamber, a particle holder 32 configured to hold a particle in the test chamber, and/or a computer system 34.

Systems 10 may be configured for use and/or may be used with any suitable type and configuration of particle, for which ignition properties are desired to be determined. For example, particles 14 may be described as small particles and may be associated with various scenarios and/or environments discussed herein. As illustrative, non-exclusive examples, a particle 14 may include a metal, a non-metal, a polymer, a grain, an organic substance, a carbon fiber, a carbon fiber reinforced plastic, a portion of a fastener, a portion of a fuel transport component, a portion of a hydraulic component, a portion of an electrical component, etc. For example, it may be desirable to acquire data associated with a small portion of metallic welding material that is ejected into a below-ground mining environment. As another illustrative and non-exclusive example, it may be desirable to acquire data associated with grain dust that is present in agricultural grain silos. Illustrative, non-exclusive examples of particle sizes that may be tested by a system 10 include (but are not limited to) particles that have a largest dimension that is in the range of 1-10000, 1-1000, 1-100, 1-10, 10-10000, 10-1000, 10-100, 100-10000, 100-1000, or 1000-10000 microns and/or that is less than 10000, 1000, 100, or 10 microns.

Similarly, systems 10 may be configured for use and/or may be used with any suitable type and configuration of gas 18 for which ignition properties are desired to be determined in relation to various particles 14. For example, gas 18 may include a combustible gas. Additionally or alternatively, gas 18 may include a non-combustible gas. It may be desirable to utilize a gas mixture of more than one gas. Various pressures of gases may be tested. As illustrative, non-exclusive examples, the pressure of the gas that is delivered to the test chamber may be in the range of 0-2, 0-1, 0-0.5, 0.5-1, or 0.2-0.5 bars. In some instances, the pressure may be less than or equal to 1 bar, while in other instances the pressure may be greater than or equal to 1 bar, depending on the specific scenario and/or environment being simulated and tested. For example, in aerospace applications, it may be desirable to simulate an environment associated with an aircraft at altitude or associated with a spacecraft in outer space. Alternatively, it may be desirable to simulate an environment associated with pressures that generally are greater than atmosphere. Accordingly, gas supply 16 may be configured to deliver gas 18 to the test chamber 12 and/or the ducting 24 at any suitable pressure, such as (but not limited to) the various ranges disclosed herein.

Various temperatures of gases may be tested. As illustrative, non-exclusive examples, the temperature of the gas that is delivered to the test chamber may be in the range of −60-200° C., depending on the specific scenario and/or environment being simulated and tested. Some systems 10 may therefore include a gas temperature control system 36 that is configured to regulate or otherwise control a desired temperature of the gas 18 in the test chamber 12. In FIG. 1, the gas temperature control system is schematically and optionally illustrated within test chamber 12 in an overlapping relationship with the gas supply 16, schematically illustrating that the regulation of gas temperature may take place in the test chamber itself, or prior to delivery of the gas to the test chamber, such as in the gas supply. Additionally or alternatively, the gas temperature may be actively regulated elsewhere in the optional ducting 24 to result in a desired temperature of the gas in the test chamber. However, active regulation of the gas temperature is not required in all systems 10, and as discussed herein, the active heating of a particle 14 may be performed to simulate the desired scenario and/or environment being tested.

The gas 18 may be delivered to the test chamber 12 at any desirable velocity relative to the particle 14. For example, in systems 10 that include a fan 28 and ducting 24, the fan may be configured to channel the gas through the ducting and around the particle in the test chamber at rates in the range of 0-1000, 0-500, 0-100, 0-10, 10-1000, 10-500, 10-100, 100-1000, 100-500, or 500-1000 meters per second (m/s) relative to the particle. Other velocities outside of these ranges also may be used and are within the scope of the present disclosure. Additionally or alternatively, such velocities may be sustained for various periods of time, for example, depending on the scenario and/or environment being simulated and tested. For example, the flow of gas around the particle may be sustained for 1-60 seconds, or for times that are less than one second or that are greater than 60 seconds.

The test chamber 12 of a system 10 may have any suitable configuration. For example, the test chamber may be sized to hold a particle 14 to be tested. Additionally or alternatively, the test chamber may be configured to maintain a substantially laminar flow of the gas 18 around the particle and/or through the test chamber during operation of a system 10. Accordingly, the test chamber may have any suitable size such that it is large enough to hold a particle to be tested, generally facilitates laminar flow of gas through the test chamber, and facilitates the use of data acquisition equipment 22. A test chamber may define an internal volume 52 that is as small as one cubic inch ($in^3$), or 15 cubic centimeters ($cm^3$), or that is as large as 2000 $in^3$, or 33000 $cm^3$. Sizes of test chambers outside of this range, including sizes that are less than and sizes that are greater than, also are within the scope of the present disclosure.

A test chamber 12 may include generally smooth walls 40 and may be free of structure that imparts turbulence to the flow of gas through the test chamber, at least in the vicinity of a particle being tested and at desired velocities of gas. Additionally or alternatively, the test chamber may be configured to permit a user to observe a particle being tested. Accordingly, a test chamber may include a window 38. In some embodiments, when present, the window may be flush with an inner surface 42 of the test chamber, so that the window does not impart turbulent flow to the gas channeled through the test chamber. The window may be sized so as to permit observation of the particle by a user. Additionally or alternatively, the window may be sized so as to permit collection of data via the window by data acquisition equipment 22. Additionally or alternatively, the window may be sized so as to permit use of a heating device 20 that is external to the test chamber for heating a particle in the test chamber. In some embodiments, the test chamber may include more than one window, such as including one for observation by a user and one for directing a heating device at the particle. Other configurations also are within the scope of the present disclosure.

In some embodiments of systems 10, the test chamber 12, as well as other components such as ducting 24, may be configured to withstand pressure impulses, such as associated with combustion of the gas and/or the particle in the test chamber, without damage, or at least without substantial damage, to component parts of the system. As an illustrative, non-exclusive example, the test chamber may be configured to withstand pressures of up to 15 bars. Additionally or alternatively, a system may be configured to withstand combustion of the gas in the test chamber if ignited by the particle. Additionally or alternatively, the walls 40 of the test chamber may be sized to withstand a pressure of up to 15 bars and/or to withstand combustion of the gas in the test chamber if ignited by the particle.

As mentioned, some systems 10 include a particle holder 32 that is configured to hold a particle 14 in the test chamber, and thus for testing the ignition properties associated with the particle and a flow of gas 18 around the particle. In some embodiments, the particle holder may be configured to hold a particle in a fixed position relative to the flow of gas around the particle. So that the particle holder does not negatively influence the laminar flow of gas in the test chamber upstream of the particle, the particle holder may be configured to position the particle upstream from the particle holder. As used herein, upstream and downstream refer to the directions associated with the flow of gas through the test chamber. Accordingly, a position upstream from a structure in the test chamber is toward a gas inlet 44 relative to such structure, and a position downstream from a structure in the test chamber is toward a gas outlet 46 relative to such structure.

An illustrative, non-exclusive example of a suitable particle holder 32 includes a rod 48 that is aligned with the flow of gas 18 around the particle. In some such embodiments, the rod may be described as a wire. Additionally or alternatively, the rod may have a diameter, or other dimension, that is less than the largest dimension of the particle 14 being held by the particle holder. Accordingly, the particle holder may facilitate laminar flow of gas through the test chamber, at least upstream of the particle. In other words, the particle holder may be configured so that it does not impact a desired flow of gas through the test chamber and around a particle being tested.

As mentioned, systems 10 include a heating device 20 that is configured to heat a particle 14 held in the test chamber 12. The heating device may take suitable form such that it is configured to selectively heat a particle to a desired temperature, such as corresponding to a scenario and/or environment being simulated and tested. Illustrative, non-exclusive examples of desired temperatures are in the range of 25-4000° C. In FIG. 1, the heating device is schematically illustrated in an overlapping relationship with the test chamber, schematically representing that the heating device may be integral with the test chamber, may be within the test chamber, may be separate and apart from the test chamber, and/or may be external to the test chamber. As illustrative, non-exclusive examples, the heating device may be configured to heat a particle held in the test chamber utilizing a laser or utilizing infra-red (IR) light. Accordingly, a heating device may be described as a laser and/or as an IR heater. In some such embodiments (although not required), the heating device may be external to the test chamber and may direct energy through an optional window 38 at a particle held in the test chamber.

Additionally or alternatively, in some embodiments, a particle holder 32 may include a heating device 20 and/or may be configured to cooperate with a heating device, such that a particle being held by the particle holder is heated via conduction through the particle holder. As an illustrative, non-exclusive example, the particle holder may include, or may be coupled to, a resistive heater and/or an induction heater. Other examples of heating devices also are within the scope of the present disclosure, and as mentioned, any suitable heating device may be utilized with a system 10 such that it is configured to selectively heat a particle to a desired temperature.

The data acquisition equipment 22 of a system 10 may include any suitable equipment, depending on the data desired to be acquired and associated with a particle 14 and gas 18 being tested. The data acquisition equipment may include equipment that is configured to capture light data over a period of time or at intervals of time. For example, a camera that captures still and/or moving images of visible light data may be used. Additionally or alternatively, the data acquisition equipment may be configured to collect temperature data associated with the particle and/or the gas being tested. Additionally or alternatively, the data acquisition equipment may be configured to collect pressure data associated with the gas in the test chamber. In some embodiments, the data acquisition equipment may be configured to measure pressure profiles of the gas around the particle. Additionally or alternatively, the data acquisition equipment may be configured to collect velocity data associated with the gas in the test chamber, including in some embodiments, velocity profiles of the gas around the particle. Additionally or alternatively, the data acquisition equipment may be configured to measure time, such as elapsed time associated with ignition of a particle in a flow of gas and/or with ignition of the gas flowing around the particle. Additionally or alternatively, the data acquisition equipment may include schlieren imaging equipment, such as equipment that is capable of detecting flow density gradients of a gas flowing around a particle in the test chamber.

In FIG. 1, the data acquisition equipment 22 is schematically illustrated in an overlapping relationship with the test chamber 12, schematically representing that the data acquisition equipment may be integral with the test chamber, may be within the test chamber, may be separate and apart from the test chamber, and/or may be external to the test chamber. Moreover, the data acquisition equipment is schematically illustrated in an overlapping relationship with the optional window 38, schematically representing that some data acquisition equipment may be configured and positioned to collect data associated with a particle and a flow gas via the optional window.

As schematically and optionally illustrated in FIG. 1, a system 10 also may include a computer system 34. In some embodiments, the computer system may be coupled to and/or may communicate with the data acquisition equipment 22. Additionally or alternatively, in some embodiments, the computer system may be configured to operate the data acquisition equipment. When present, a computer system may be utilized for maintaining a database associated with ignition properties of particles tested by a system 10 and based at least in part on data acquired by the data acquisition equipment. The optional computer system may be described as including non-transitory computer readable storage media configured with such a database.

When utilized, the database may include data associated with different particles having different sizes, having different temperatures, having different material compositions, etc. Additionally or alternatively, the database may include data associated with different gases or gas mixtures, different velocities of flows of gases, different temperatures of flows of gases, and different pressures of flows of gases that were utilized to test particles by a system 10. Accordingly, such a database may be described as defining, and/or may be used to define, various models associated with various particles and gases, such as corresponding to various scenarios and environments. Over a period of time, such models may be robust enough to predict the ignition properties associated with a given particle and a given gas associated with a given environment. As a result, it may not be necessary to actually utilize a system 10 according to the present disclosure to physically test a particular particle and a particular flow of gas to determine, or otherwise predict, the ignition properties associated with the particular particle and flow of gas.

As mentioned, a system 10 may include ducting 24 that defines a closed-loop conduit 26 that includes the test chamber 12 and a fan 28 that is configured to channel gas 18 through the ducting and around a particle 14 in the test chamber. Such a system 10 may be described as, or as including, a closed-loop wind tunnel 50 that includes at least the ducting, the test chamber, and the fan and that is configured to recirculate a flow of gas through the test chamber and around the closed-loop conduit 26 for purposes of testing the ignition properties associated with a particle and a gas. As used herein, a fan includes any suitable structure and mechanism for imparting a flow to the gas 18 around the closed-loop conduit. A turbine is an illustrative, non-exclusive example of a suitable fan, but other types and configurations of fans may be utilized by a system 10.

In some embodiments, the wind tunnel 50 may include various structures that are configured to facilitate laminar flow of gas 18 around the closed-loop conduit 26. As an illustrative, non-exclusive example, a wind tunnel may include structures 54, such as louvers, that are configured to facilitate laminar flow of the gas around bends or corners in the closed-loop conduit. Additionally or alternatively, a wind tunnel may include one or more screens 56 having a mesh size that facilitates laminar flow of the gas around the closed-loop conduit. Additionally or alternatively, the optional screens 56 may prevent, or at least restrict, the detonation of gas 18, at least within conditions being tested by a system 10.

Some systems 10 may incorporate a vacuum system 30 that is configured to draw a vacuum in the test chamber 12 and/or in the closed-loop conduit 26, when present, such as to remove any air that is present. Accordingly, the gas supply 16 may subsequently introduce gas 18 into the test chamber and/or the closed-loop conduit, when present, to achieve a desired pressure of the gas based on the scenario and/or environment being tested and simulated.

Turning now to the flowchart of FIG. 2, methods 100 are schematically represented. As mentioned, a method 100 is not required to utilize a system 10, and a system 10 is not required to perform or otherwise implement a method 100. However, it is within the scope of the present disclosure that a system 10 may utilize and/or otherwise be associated with a method 100, and method 100 may be performed with, or at least partially with, a system 10.

As schematically illustrated in FIG. 2, a method 100 for testing ignition properties of particles may include generating a flow of gas around a particle that is fixed in space relative to the flow of gas in a test chamber, as indicated at 102, heating the particle and/or the gas to a desired temperature, as indicated at 104, and collecting data associated with the particle and/or the flow of gas, as indicated at 106.

In some methods 100, the generating 102 may include drawing a vacuum and inserting a volume of gas to achieve a predetermined, or desired, pressure of the gas, and imparting the flow to the gas. Additionally or alternatively, the generating may include maintaining a substantial laminar flow of the gas around the particle. Additionally or alternatively, the generating may be facilitated by a closed-loop wind tunnel that includes the test chamber. Additionally or alternatively, the generating may include recirculating the gas through the test chamber.

In some methods 100, the heating 104 may include heating the particle with a laser. Additionally or alternatively, the heating may include heating the particle with infra-red light. Additionally or alternatively, the heating may include conducting heat from a particle holder. Additionally or alternatively, the heating may include resistive heating and/or induction heating. Additionally or alternatively, the heating may include heating the particle to a temperature in the range of 25-4000° C.

In some methods, the collecting 106 may include visually observing and/or visually recording the particle. Additionally or alternatively, the collecting may include measuring the temperature of the particle and/or the temperature of the gas. Additionally or alternatively, the collecting may include measuring a velocity of the flow of gas around the particle, and in some methods, measuring a velocity profile of the flow of gas around the particle. Additionally or alternatively, the collecting may include measuring the pressure of the flow of gas, and in some methods, measuring a pressure profile of the flow of gas around the particle. Additionally or alternatively, the collecting may include collecting time data, such as including elapsed time associated with ignition of the particle in the flow of gas and/or ignition of the gas around the particle. Additionally or alternatively, the collecting may include collecting schlieren images associated with the flow of gas around the particle.

As schematically and optionally illustrated in FIG. 2, some methods 100 also may include storing the data in a database, as indicated at 108. In some such methods, the generating, the eating, and collecting, and the storing may be repeated, as schematically indicated at 110, such as for different particles. For example, the different particles may have different sizes and/or they may have different material compositions. Additionally or alternatively, the repeating 110 may be performed for different gases or gas mixtures. Additionally or alternatively, the repeating may be performed with different velocities of the flow of gas around the particle. Additionally or alternatively, the repeating may be performed with different pressures of the flow of gas around the particle. Additionally or alternatively, the repeating may be performed with different temperatures of the flow of gas around the particle.

Some methods 100 also may include accessing the database for engineering an environment, as indicated optionally at 112. As indicated at 114, a method according to the present disclosure also may include engineering the environment based at least in part on the accessing 112. In other words, the database of ignition properties associated with particles and gases may be accessed by engineers to design and develop various environments in which a risk of a particle being emitted into a volume of gas is present. For example, the database may be accessed by aerospace engineers when engineering an aircraft fuel system. Additionally or alternatively, the database may be accessed by agricultural engineers when engineering grain silos. Other examples also are within the scope of the present disclosure.

Figure 3:
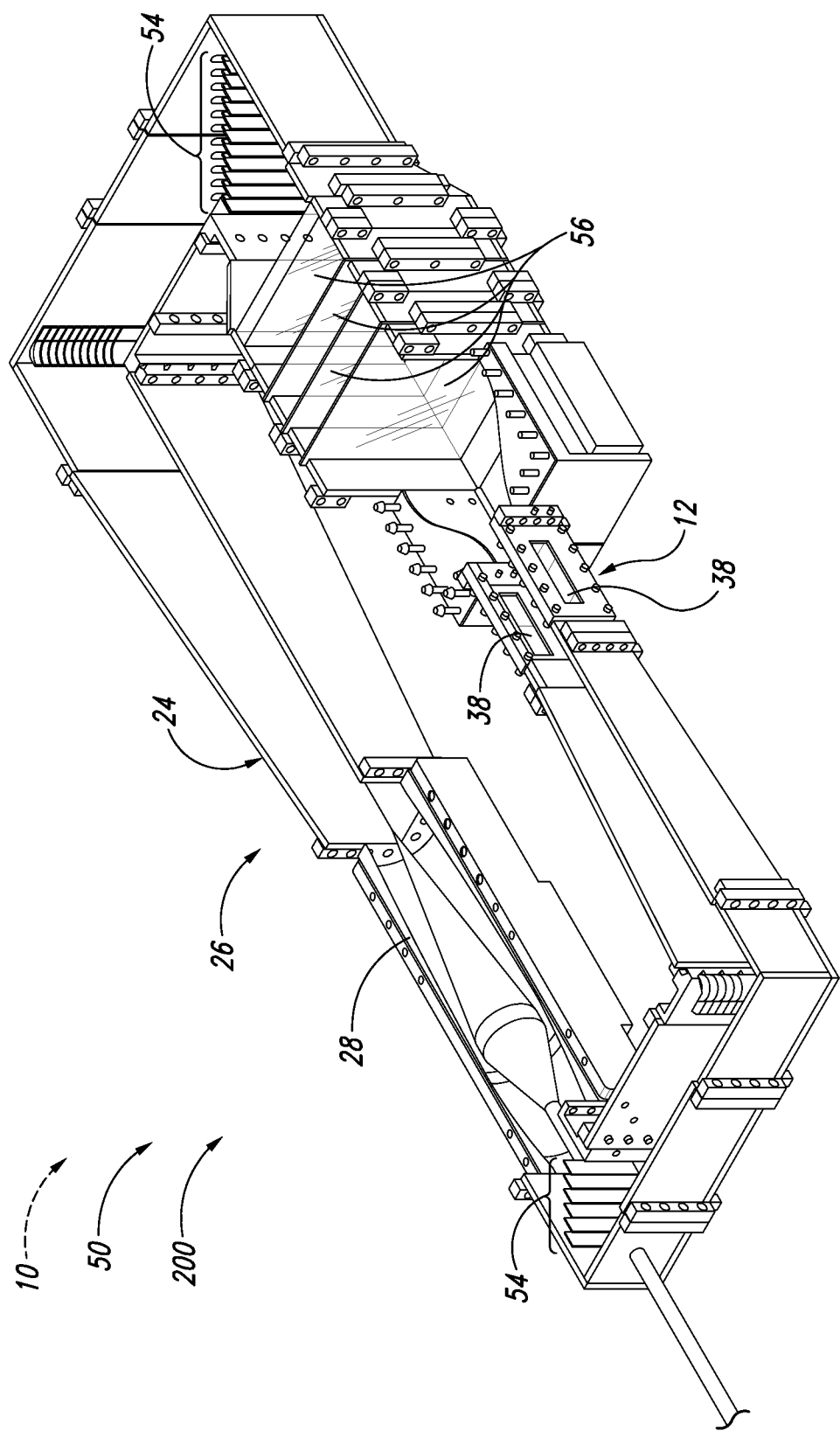
FIG. 3 is an isometric cross-sectional view of an illustrative, non-exclusive example of a system for testing ignition properties of particles.

Turning now to FIG. 3, an illustrative non-exclusive example of a closed-loop wind tunnel 50 that may be used in a system 10 and/or for facilitating a method 100 is illustrated, with the example wind tunnel indicated generally at 200. Where appropriate, the reference numerals from the schematic illustration of FIG. 1 are used to designate corresponding parts of wind tunnel 200; however, the example of FIG. 3 is non-exclusive and does not limit systems 10, wind tunnels 50, an/or methods 100 to utilizing the illustrated embodiments of wind tunnel 200.

In FIG. 3, the wind tunnel 200 is illustrated in cross-section to reveal various internal structures thereof. As seen, wind tunnel 200 includes ducting 24 that defines a closed-loop conduit 26 including a test chamber 12 that has two windows 38. A fan 28 is provided to recirculate gas around the closed-loop conduit and through the test chamber. Downstream of the test chamber, a series of screens 56 are provided to facilitate laminar flow through the ducting and to prevent, or at least restrict, detonation of gas within the ducting. The wind tunnel also includes structures 54 in the form of louvers that are configured to facilitate laminar flow of gas around corners in the closed-loop conduit.

Illustrative, non-exclusive examples of inventive subject matter according to the present disclosure are described in the following enumerated paragraphs:

A. A method for testing ignition properties of particles, the method comprising:

generating a flow of a gas around a particle that is fixed in space relative to the flow of the gas in a test chamber;

heating the particle and/or heating the gas to a temperature; and collecting data associated with the particle and/or the flow of the gas.

A1. The method of paragraph A, wherein the gas, the particle, and the temperature correspond to a predefined scenario to be simulated.

A1.1. The method of paragraph A1, wherein the predefined scenario to be simulated includes one or more of an aerospace scenario, an industrial scenario, a mining scenario, an agricultural scenario, a scenario associated with fuel fumes, a scenario associated with combustible gases, a scenario associated with hot particles, and/or a scenario associated with a hot particle moving through a gas.

A2. The method of any of paragraphs A-A1.1, wherein the gas includes a combustible gas, optionally wherein the gas consists of a combustible gas, and optionally wherein the gas consists essentially of a combustible gas.

A3. The method of any of paragraphs A-A2, wherein the gas includes a non-combustible gas, optionally wherein the gas consists of a non-combustible gas, and optionally wherein the gas consists essentially of a non-combustible gas.

A4. The method of any of paragraphs A-A3, wherein the gas includes a gas mixture.

A5. The method of any of paragraphs A-A4, wherein the flow of the gas is at a rate in the range of 0-1000, 0-500, 0-100, 0-10, 10-1000, 10-500, 10-100, 100-1000, 100-500, or 500-1000 m/s relative to the particle.

A6. The method of any of paragraphs A-A5, wherein the flow of the gas is at a pressure in the range of 0-2, 0-1, 0-0.5, 0.5-1, or 0.2-0.5 bars, at a pressure that is less than or equal to 1 bar, and/or at a pressure that is greater than or equal to 1 bar.

A7. The method of any of paragraphs A-A6, wherein the heating the gas includes heating the gas to a temperature of up to 200° C.

A8. The method of any of paragraphs A-A7, wherein the generating the flow of the gas includes drawing a vacuum within the test chamber, inserting a volume of gas into the test chamber to achieve a predetermined pressure of the gas, and imparting the flow to the gas.

A9. The method of any of paragraphs A-A8, wherein the generating the flow of the gas includes maintaining a substantial laminar flow of the gas in the test chamber.

A10. The method of any of paragraphs A-A9, wherein the generating the flow of the gas is facilitated by a closed-loop wind tunnel that includes the test chamber.

A11. The method of any of paragraphs A-A10, wherein the generating the flow of the gas includes recirculating the gas through the test chamber.

A12. The method of any of paragraphs A-A11, wherein the particle has a largest dimension in the range of 1-10000, 1-1000, 1-100, 1-10, 10-10000, 10-1000, 10-100, 100-10000, 100-1000, or 1000-10000 microns and/or less than 10000, 1000, 100, or 10 microns.

A13. The method of any of paragraphs A-A12, wherein the particle includes, consists of, and/or consists essentially of a metal, a non-metal, a polymer, a grain, an organic substance, a carbon fiber, a carbon fiber reinforced plastic, a portion of a fastener, a portion of a fuel transport component, a portion of a hydraulic component, or a portion of an electrical component.

A14. The method of any of paragraphs A-A13, wherein the heating the particle includes heating the particle with a laser.

A15. The method of any of paragraphs A-A14, wherein the heating the particle includes heating the particle with infra-red light.

A16. The method of any of paragraphs A-A15, wherein the heating the particle includes conducting heat from a particle holder.

A17. The method of any of paragraphs A-A16, wherein the heating the particle includes heating the particle to a temperature in the range of 25-4000° C.

A18. The method of any of paragraphs A-A17, wherein the collecting data includes visually observing and/or recording the particle.

A19. The method of any of paragraphs A-A18, wherein the collecting data includes measuring the temperature of the particle and/or the temperature of the gas.

A20. The method of any of paragraphs A-A19, wherein the collecting data includes measuring a velocity of the flow of the gas around the particle, and optionally measuring a velocity profile of the flow of the gas around the particle.

A21. The method of any of paragraphs A-A20, wherein the collecting data includes measuring a pressure of the flow of the gas, and optionally measuring a pressure profile of the flow of the gas around the particle.

A22. The method of any of paragraphs A-A21, wherein the collecting data includes collecting time data, optionally wherein the time data includes elapsed time associated with ignition of the particle in the flow of the gas and/or ignition of the gas around the particle.

A23. The method of any of paragraphs A-A22, wherein the collecting data includes collecting schlieren images associated with the flow of the gas around the particle.

A24. The method of any of paragraphs A-A23, further comprising:

storing the data in a database.

A24.1. The method of paragraph A24, further comprising:

repeating the generating, the heating, the collecting, and the storing for different particles, optionally wherein the different particles have different sizes, optionally wherein the different particles are comprised of, consist of, and/or consist essentially of different materials.

A24.2. The method of any of any of paragraphs A24-A24.1, further comprising:

repeating the generating, the heating, the collecting, and the storing for different gases or gas mixtures.

A24.3. The method of any of paragraphs A24-A24.2, further comprising:

repeating the generating, the heating, the collecting, and the storing with different velocities of the flow of gas around the particle.

A24.4. The method of any of paragraphs A24-A24.3, further comprising:

repeating the generating, the heating, the collecting, and the storing with different pressures of the flow of the gas around the particle.

A24.5. The method of any of paragraphs A24-A24.4, further comprising:

repeating the generating, the heating, the collecting, and the storing with different temperatures of the gas and/or the particle.

A24.6. The method of any of paragraphs A24-A24.5, further comprising:

accessing the database for engineering an environment, optionally wherein the environment includes one or more of an aerospace environment, an industrial environment, a mining environment, an agricultural environment, an environment associated with fuel fumes, an environment associated with combustible gases, and/or an environment associated with hot particles.

A24.6.1. A method, comprising:
performing the method of paragraph A24.6; and
engineering the environment based at least in part on the accessing.

A25. The method of any of paragraphs A-A24.6.1, further comprising:
cooling the gas to a gas temperature and heating the particle to a particle temperature.

A26. The method of any of paragraphs A-A25 utilizing the system of any of paragraphs B-B28.

B. A testing system for testing ignition properties of particles, the testing system comprising:
a test chamber sized to hold a particle to be tested;
a gas supply configured to deliver a gas to the test chamber;
a heating device configured to heat the particle; and
data acquisition equipment configured to collect data associated with the particle and/or the gas.

B1. The testing system of paragraph B, further comprising:
ducting that defines a closed-loop conduit that includes the test chamber; and a fan configured to channel the gas through the ducting and around the particle in the test chamber.

B1.1. The testing system of paragraph B1, wherein the fan is configured to channel the gas through the ducting and around the particle in the test chamber at a rate in the range of 0-1000, 0-500, 0-100, 0-10, 10-1000, 10-500, 10-100, 100-1000, 100-500, or 500-1000 m/s relative to the particle.

B2. The testing system of any of paragraphs B-B1.1, wherein the gas and the particle correspond to a predefined scenario to be simulated.

B2.1. The testing system of paragraph B2, wherein the predefined scenario to be simulated includes one or more of an aerospace scenario, an industrial scenario, a mining scenario, an agricultural scenario, a scenario associated with fuel fumes, a scenario associated with combustible gases, a scenario associated with hot particles, and/or a scenario associated with a hot particle moving through a gas.

B3. The testing system of any of paragraphs B-B2.1, wherein the gas includes a combustible gas, optionally wherein the gas consists of a combustible gas, and optionally wherein the gas consists essentially of a combustible gas.

B4. The testing system of any of paragraphs B-B2.1, wherein the gas includes a non-combustible gas, optionally wherein the gas consists of a non-combustible gas, and optionally wherein the gas consists essentially of a non-combustible gas.

B5. The testing system of any of paragraphs B-B4, wherein the gas includes a gas mixture.

B6. The testing system of any of paragraphs B-B5, wherein the gas supply is configured to deliver the gas to the test chamber at a pressure in the range of 0-2, 0-1, 0-0.5, 0.5-1, or 0.2-0.5 bars, at a pressure that is less than or equal to 1 bar, and/or at a pressure that is greater than or equal to 1 bar.

B7. The testing system of any of paragraphs B-B6, further comprising:
the gas in the test chamber, wherein the gas is at a pressure in the range of 0-2, 0-1, 0-0.5, 0.5-1, or 0.2-0.5 bars, at a pressure that is less than or equal to 1 bar, and/or at a pressure that is greater than or equal to 1 bar.

B8. The testing system of any of paragraphs B-B7, further comprising:
the gas in the test chamber, wherein the gas is at a temperature in the range of −60-200° C.

B9. The testing system of any of paragraphs B-B8, further comprising:
a gas temperature control system configured to control a temperature of the gas in the test chamber.

B10. The testing system of any of paragraphs B-B9, further comprising:
a vacuum system configured to draw a vacuum in the test chamber and/or a/the closed-loop conduit.

B11. The testing system of any of paragraphs B-B10, wherein the test chamber is configured to maintain a substantially laminar flow of the gas around the particle and/or through the test chamber.

B12. The testing system of any of paragraphs B-B11, further comprising:
the particle to be tested, wherein the particle is held in the test chamber, and wherein the particle has a largest dimension in the range of 1-10000, 1-1000, 1-100, 1-10, 10-10000, 10-1000, 10-100, 100-10000, 100-1000, or 1000-10000 microns and/or less than 10000, 1000, 100, or 10 microns.

B12.1. The testing system paragraph B12, wherein the particle includes, consists of, and/or consists essentially of a metal, a non-metal, a polymer, a grain, an organic substance, a carbon fiber, a carbon fiber reinforced plastic, a portion of a fastener, a portion of a fuel transport component, a portion of a hydraulic component, or a portion of an electrical component.

B13. The testing system of any of paragraphs B-B12.1, wherein the heating device is configured to heat the particle with a laser.

B14. The testing system of any of paragraphs B-B13, wherein the heating device is configured to heat the particle with infra-red light.

B15. The testing system of any of paragraphs B-B14, further comprising:
a particle holder configured to hold the particle in the test chamber in a fixed position relative to a flow of the gas around the particle.

B15.1. The testing system of paragraph B15, wherein the heating device is configured to heat the particle via conduction from the particle holder, optionally via resistive heating and/or induction heating.

B15.2. The testing system of any of paragraphs B15-B15.1, wherein the particle holder is configured to position the particle upstream relative to the particle holder.

B15.3. The testing system of any of paragraphs B15-B15.2, wherein the particle holder is configured to facilitate laminar flow of the gas around the particle and/or upstream of the particle.

B15.4. The testing system of any of paragraphs B15-B15.3, wherein the particle holder includes a rod aligned with a direction of the flow of the gas around the particle.

B16. The testing system of any of paragraphs B-B15.4, wherein the test chamber includes a window positioned to facilitate visual observation of the particle to be tested.

B16.1. The testing system of paragraph B16, wherein the window is configured to facilitate laminar flow of the gas in the test chamber.

B16.2. The testing system of any of paragraphs B16-B16.1, wherein the window is flush with an inner surface of the test chamber.

B16.3. The testing system of any of paragraphs B16-B16.2, wherein the heating device is positioned outside of the test chamber and is configured to heat the particle through the window.

B17. The testing system of any of paragraphs B-B16.3, wherein the data acquisition equipment includes equipment that is configured to capture light data over time.

B18. The testing system of any of paragraphs B-B17, wherein the data acquisition equipment is configured to measure a temperature of the particle.

B19. The testing system of any of paragraphs B-B18, wherein the data acquisition equipment is configured to measure a temperature of the gas in the test chamber.

B20. The testing system of any of paragraphs B-B19, wherein the data acquisition equipment is configured to measure a pressure of the gas in the test chamber, optionally a pressure profile of the gas around the particle.

B21. The testing system of any of paragraphs B-B20, wherein the data acquisition equipment is configured to measure a velocity of the gas in the test chamber, optionally a velocity profile of the gas around the particle.

B22. The testing system of any of paragraphs B-B21, wherein the data acquisition equipment is configured to collect time data, optionally wherein the time data includes elapsed time associated with ignition of the particle in the gas and/or ignition of the gas around the particle.

B23. The testing system of any of paragraphs B-B22, wherein the data acquisition equipment includes schlieren imaging equipment.

B24. The testing system of any of paragraphs B-B23, further comprising:

a computer system including non-transitory computer readable storage media configured with a database for maintaining data associated with ignition properties of particles tested by the testing system and based at least in part on data acquired from the data acquisition equipment.

B24.1. The testing system of paragraph B24, wherein the database includes data associated with different particles having different sizes, having different temperatures, and/or including, consisting of, and/or consisting essentially of different materials.

B24.2. The testing system of any of paragraphs B24-B24.1, wherein the database includes data associated with different gases or gas mixtures utilized to test particles by the testing system.

B24.3. The testing system of any of paragraphs B24-B24.2, wherein the database includes data associated with different velocities of flows of gases utilized to test particles by the testing system.

B24.4. The testing system of any of paragraphs B24-B24.3, wherein the database includes data associated with different temperatures of flows of gases utilized to test particles by the testing system.

B24.5. The testing system of any of paragraphs B24-B24.6, wherein the database includes data associated with different pressures of flows of gases utilized to test particles by the testing system.

B25. The testing system of any of paragraphs B-B24.5, wherein the system is configured to withstand a pressure of up to 15 bars in the test chamber, optionally without damage to the system.

B26. The testing system of any of paragraphs B-B25, wherein the system is configured to withstand combustion of the gas in the test chamber if ignited by the particle, optionally without damage to the system.

B27. The testing system of any of paragraphs B-B26, wherein the test chamber is defined by walls that are sized to withstand a pressure of up to 15 bars and/or to withstand combustion of the gas in the test chamber if ignited by the particle, optionally without damage of the system.

B28. The testing system of any of paragraphs B-B27 configured to facilitate at least in part the method of any of paragraphs A-A26.

B29. The use of the testing system of any of paragraphs B-B28.

As used herein, the terms "selective" and "selectively," when modifying an action, movement, configuration, or other activity of one or more components or characteristics of an apparatus, mean that the specific action, movement, configuration, or other activity is a direct or indirect result of user manipulation of an aspect of, or one or more components of, the apparatus.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A method for testing ignition properties of particles, the method comprising:
generating a flow of a gas around a particle that is fixed in space relative to the flow of the gas in a test chamber, wherein the particle is in the flow of the gas;
heating the particle to a desired temperature; and
collecting data associated with the particle and the flow of the gas.

2. The method of claim 1, further comprising selecting the gas, the flow of the gas, the particle and the desired temperature to correspond to a predefined scenario to be simulated, wherein the predefined scenario to be simulated includes a scenario associated with a hot particle moving through a gas.

3. The method of claim 2, wherein the predefined scenario to be simulated includes an aerospace scenario.

4. The method of claim 1, wherein the gas is a combustible gas.

5. The method of claim 4, wherein the heating results in combustion of the combustible gas, and wherein the collecting data includes collecting data associated with the combustion of the combustible gas.

6. The method of claim 1, wherein the gas consists essentially of a non-combustible gas.

7. The method of claim 1, wherein the flow of the gas is at a rate in the range of 0-500 m/s relative to the particle.

8. The method of claim 1, wherein the flow of the gas is at a pressure that is less than 1 bar.

9. The method of claim 1, wherein the generating the flow of the gas includes drawing a vacuum within the test chamber, inserting a volume of the gas into the test chamber to achieve a predetermined pressure of the gas, and imparting the flow to the gas.

10. The method of claim 1, wherein the generating the flow of the gas is facilitated by a closed-loop wind tunnel that includes the test chamber.

11. The method of claim 1, wherein the generating the flow of the gas includes recirculating the gas through the test chamber.

12. The method of claim 1, wherein the particle has a largest dimension in the range of 10-1000 microns.

13. The method of claim 1, wherein the particle is a metallic particle.

14. The method of claim 1, wherein the heating the particle includes heating the particle with a laser.

15. The method of claim 1, wherein the heating the particle includes heating the particle with infra-red light.

16. The method of claim 1, wherein the heating the particle includes conducting heat from a particle holder.

17. The method of claim 1, wherein the desired temperature is in the range of 25-4000° C.

18. The method of claim 1, wherein the collecting data includes one or more of visually observing the particle, visually recording the particle, measuring a temperature of the particle, measuring a velocity of the flow of the gas around the particle, measuring a pressure of the flow of gas, collecting time data, and collecting schlieren images associated with the flow of the gas around the particle.

19. The method of claim 1, further comprising:
storing the data in a database; and
repeating the generating, the heating, the collecting, and the storing for different particles, wherein the different particles have different sizes or are comprised of different materials.

20. The method of claim 1, further comprising:
storing the data in a database; and
repeating the generating, the heating, the collecting, and the storing for different gases.

21. The method of claim 1, further comprising:
storing the data in a database; and
repeating the generating, the heating, the collecting, and the storing with one or more of different velocities of the flow of the gas around the particle, different pressures of the flow of the gas around the particle, and different temperatures of the particle.

22. The method of claim 1, wherein the generating the flow of the gas includes maintaining a laminar flow of the gas in the test chamber with the particle in the laminar flow of the gas.

23. The method of claim 1, wherein the generating the flow of the gas is facilitated by a closed-loop wind tunnel that includes the test chamber, and wherein the generating the flow of the gas includes:
drawing a vacuum within the test chamber;
inserting a volume of the gas into the test chamber to achieve a predetermined pressure of the gas;
imparting the flow to the gas;
recirculating the gas through the test chamber; and
maintaining a laminar flow of the gas in the test chamber with the particle in the laminar flow of the gas.

24. A method for testing ignition properties of particles, the method comprising:
generating a flow of a combustible gas around a particle that is fixed in space relative to the flow of the combustible gas in a test chamber, wherein the flow of the combustible gas is at a pressure that is less than 1 bar, wherein the particle is in the flow of the combustible gas, and wherein the particle has a largest dimension in the range of 10-1000 microns;
heating the particle to a desired temperature;
collecting data associated with the particle and the flow of the combustible gas;
storing the data in a database; and
repeating the generating, the heating, the collecting, and the storing for different particles and with different gases, wherein the different particles are comprised of different materials.

25. A testing system for testing ignition properties of particles, the testing system comprising:
a test chamber sized to hold a particle to be tested;
a gas supply configured to deliver a gas to the test chamber;
a particle holder configured to hold the particle in a flow of gas in the test chamber and to hold the particle in a fixed position relative to the flow of gas around the particle;
a heating device configured to heat the particle to a desired temperature; and
data acquisition equipment configured to collect data associated with the particle and/or the gas.

* * * * *